(12) United States Patent
Cole (10) Patent No.: US 7,656,532 B2
(45) Date of Patent: Feb. 2, 2010

(54) CAVITY RING-DOWN SPECTROMETER HAVING MIRROR ISOLATION

(75) Inventor: Barrett E. Cole, Bloomington, MN (US)

(73) Assignee: Honeywell International Inc., Morristown, NJ (US)

(*) Notice: Subject to any disclaimer, the term of this patent is extended or adjusted under 35 U.S.C. 154(b) by 490 days.

(21) Appl. No.: 11/735,689

(22) Filed: Apr. 16, 2007

(65) Prior Publication Data

US 2007/0242266 A1    Oct. 18, 2007

Related U.S. Application Data

(60) Provisional application No. 60/793,279, filed on Apr. 18, 2006.

(51) Int. Cl.
*G01N 21/00* (2006.01)

(52) U.S. Cl. ..................... 356/432; 356/435

(58) Field of Classification Search .......... 356/432–444
See application file for complete search history.

(56) References Cited

U.S. PATENT DOCUMENTS

| | | | |
|---|---|---|---|
| 4,233,568 A | 11/1980 | Hamerdinger et al. |
| 4,612,647 A | 9/1986 | Norvell |
| 4,614,961 A | 9/1986 | Khan et al. |
| 4,870,224 A | 9/1989 | Smith et al. |
| 4,973,131 A | 11/1990 | Carnes |
| 5,022,745 A | 6/1991 | Zayhowski et al. |
| 5,040,895 A | 8/1991 | Laurent et al. |
| 5,135,304 A | 8/1992 | Miles et al. |
| 5,146,465 A | 9/1992 | Khan et al. |
| 5,278,435 A | 1/1994 | Van Hove |

(Continued)

FOREIGN PATENT DOCUMENTS

DE    3311808    10/1984

(Continued)

OTHER PUBLICATIONS

Campargue et al., "Measurement of SiH2 density in a discharge by intracavity laser absorption spectroscopy and CW cavity ring-down spectroscopy," Journal of Physics D. Applied Physics, vol. 31, No. 10 pp. 1168-1175, May 21, 1998.

(Continued)

*Primary Examiner*—Gregory J Toatley, Jr.
*Assistant Examiner*—Jarreas C Underwood
(74) *Attorney, Agent, or Firm*—Kris T. Fredrick (57) ABSTRACT

A cavity ring-down spectrometer having a light-conveying structure, a mirror and an isolator. The structure may form a resonator cavity, and the resonator cavity may include a sample sub-cavity and a mirror sub-cavity. A preconcentrator medium may be within a sample sub-cavity, and the medium may adsorb a sample substance entering the sample sub-cavity. A heater may heat the medium to desorb the sample through which a light can propagate. The mirror may be within the mirror sub-cavity, and the mirror may direct light through the mirror sub-cavity and the sample sub-cavity. The isolator may reduce, inhibit or prevent the sample substance in the sample sub-cavity from entering the mirror sub-cavity and affecting the mirror in the mirror sub-cavity.

20 Claims, 5 Drawing Sheets

U.S. PATENT DOCUMENTS

| | | | |
|---|---|---|---|
| 5,408,319 A | 4/1995 | Halbout et al. | |
| 5,418,868 A | 5/1995 | Cohen et al. | |
| 5,450,053 A | 9/1995 | Wood | |
| 5,468,910 A | 11/1995 | Knapp et al. | |
| 5,512,750 A | 4/1996 | Yanka et al. | |
| 5,528,040 A * | 6/1996 | Lehmann | 250/343 |
| 5,550,373 A | 8/1996 | Cole et al. | |
| 5,629,951 A | 5/1997 | Chang-Hasnain et al. | |
| 5,677,538 A | 10/1997 | Moustakas et al. | |
| 5,679,965 A | 10/1997 | Schetzina | |
| 5,723,706 A | 3/1998 | Brasier et al. | |
| 5,739,554 A | 4/1998 | Edmond et al. | |
| 5,834,331 A | 11/1998 | Razeghi | |
| 5,847,397 A | 12/1998 | Moustakas | |
| 5,869,896 A | 2/1999 | Baker et al. | |
| 5,900,650 A | 5/1999 | Nitta | |
| 5,909,280 A | 6/1999 | Zavracky | |
| 5,912,740 A * | 6/1999 | Zare et al. | 356/437 |
| 5,915,051 A | 6/1999 | Damask et al. | |
| 5,933,565 A | 8/1999 | Diebold | |
| 5,960,025 A | 9/1999 | Thorland et al. | |
| 6,080,988 A | 6/2000 | Ishizuya et al. | |
| 6,084,682 A * | 7/2000 | Zare et al. | 356/437 |
| 6,091,504 A | 7/2000 | Walker et al. | |
| 6,115,122 A | 9/2000 | Bao et al. | |
| 6,122,416 A | 9/2000 | Ooba et al. | |
| 6,147,756 A | 11/2000 | Zavracky et al. | |
| 6,208,798 B1 | 3/2001 | Morozov et al. | |
| 6,287,940 B1 | 9/2001 | Cole et al. | |
| 6,295,130 B1 | 9/2001 | Sun et al. | |
| 6,296,779 B1 | 10/2001 | Clark et al. | |
| 6,310,904 B1 | 10/2001 | Thorland et al. | |
| 6,324,192 B1 | 11/2001 | Tayebati | |
| 6,335,669 B1 | 1/2002 | Miyazaki et al. | |
| 6,377,350 B1 * | 4/2002 | Paldus et al. | 356/454 |
| 6,380,531 B1 | 4/2002 | Sugihwo et al. | |
| 6,384,953 B1 | 5/2002 | Russell et al. | |
| 6,404,648 B1 | 6/2002 | Slupe et al. | |
| 6,406,578 B1 | 6/2002 | Schober et al. | |
| 6,421,127 B1 | 7/2002 | McAndrew et al. | |
| 6,438,149 B1 | 8/2002 | Tayebati et al. | |
| 6,452,680 B1 | 9/2002 | Paldus et al. | |
| 6,483,130 B1 | 11/2002 | Yang et al. | |
| 6,483,149 B1 | 11/2002 | Mosher et al. | |
| 6,492,726 B1 | 12/2002 | Quek et al. | |
| 6,507,107 B2 | 1/2003 | Vaiyapuri | |
| 6,545,739 B1 | 4/2003 | Matsumoto et al. | |
| 6,583,917 B2 | 6/2003 | Melloni et al. | |
| 6,584,126 B2 | 6/2003 | Wang et al. | |
| 6,590,710 B2 | 7/2003 | Hara et al. | |
| 6,594,059 B2 | 7/2003 | Flanders | |
| 6,597,713 B2 | 7/2003 | Ouchi | |
| 6,608,711 B2 | 8/2003 | Flanders et al. | |
| 6,627,983 B2 | 9/2003 | Tu et al. | |
| 6,658,034 B2 | 12/2003 | Garnache et al. | |
| 6,670,559 B2 | 12/2003 | Centola et al. | |
| 6,728,286 B2 | 4/2004 | Thorland et al. | |
| 6,836,501 B2 | 12/2004 | Cox et al. | |
| 6,879,014 B2 | 4/2005 | Wagner et al. | |
| 6,985,281 B2 | 1/2006 | Wagner et al. | |
| 7,002,697 B2 | 2/2006 | Domash et al. | |
| 7,012,696 B2 | 3/2006 | Orr et al. | |
| 7,015,457 B2 | 3/2006 | Cole et al. | |
| 7,049,004 B2 | 5/2006 | Domash et al. | |
| 7,106,763 B2 * | 9/2006 | Tan et al. | 372/9 |
| 7,113,286 B2 | 9/2006 | Yan | |
| 7,145,165 B2 | 12/2006 | Cox et al. | |
| 7,147,165 B2 | 12/2006 | Mongin et al. | |
| 7,221,827 B2 | 5/2007 | Domash et al. | |
| 7,304,799 B2 | 12/2007 | Ma et al. | |
| 2002/0191268 A1 | 12/2002 | Seeser et al. | |
| 2003/0107739 A1 | 6/2003 | Lehmann et al. | |
| 2004/0194628 A1 | 10/2004 | Mitra | |
| 2004/0234198 A1 | 11/2004 | Wagner et al. | |
| 2004/0255853 A1 | 12/2004 | Ma et al. | |
| 2005/0030628 A1 | 2/2005 | Wagner et al. | |
| 2005/0040337 A1 | 2/2005 | Cox et al. | |
| 2005/0082480 A1 | 4/2005 | Wagner et al. | |
| 2005/0092067 A1 | 5/2005 | Petrovic et al. | |
| 2005/0105184 A1 | 5/2005 | Ma et al. | |
| 2005/0254056 A1 | 11/2005 | Kachanov et al. | |

FOREIGN PATENT DOCUMENTS

| | | |
|---|---|---|
| DE | 19635421 | 12/1997 |
| EP | 0177918 | 4/1986 |
| EP | 0667548 | 8/1995 |
| EP | 1061618 | 12/2000 |
| EP | 1069658 | 1/2001 |
| JP | 03252172 | 11/1991 |
| JP | 05095130 | 4/1993 |
| JP | 07288334 | 10/1995 |
| WO | WO 9326049 | 12/1993 |
| WO | WO 9942875 | 8/1999 |

OTHER PUBLICATIONS

Bernstein et al., "Development of a Miniature Silicon PhotoAcoustic Gas Sensor", Presented at Opto 96, Leipzig, Germany, Sep. 26-29, 1999, 6 pages.

Brown, J. et al., "Visible-Blind UV Digital Camera Based on a 32*32 Array of GAN/AlGAN P-I-N Photodiodes", MRS Internet Journal of Nitride Semiconductor Research, vol. 4S1, Sep. 1999, XP000949328 ISSN: 1092-5783.

Chitica et al., "Monolithic InP-Based Tunable Filter with 10-nm Bandwidth for Optical Data Interconnects in the 1550-nm Band," IEEE Photonics Technology Letters, vol. 11, No. 5, pp. 584-586, May 1999.

Chou et al., "Diode-Laser Measurements of He-, Ar-, and N2-Broadened HF Lineshapes in the First Overtone Band," Journal of Molecular Spectroscopy 196, pp. 70-76, 1999.

Chung et al., "Design and fabrication of 10×10 micro-spatial light modulator array for phase and amplitude modulation," Sensors and Actuators, vol. 78 No. 1, pp. 63-70, Jan. 1999.

Cole et al., "Microscopic Spectroscopy of Optical MEMS Devices," Topic 2 (Materials and Technology), Honeywell Laboratories, 2 page abstract, submitted on or around Dec. 11, 2000.

Ferber et al., "A Miniature Silicon Photoacoustic Detector for Gas Monitoring Applications", presented at the MTEX 2001 International Conference on Sensors and Transducers, Birmingham, UK, Feb. 14, 2001, 7 pages.

Jerman et al., "A miniature Fabry-Perot interferometer with a corrugated silicon diaphragm support," Sensors and Actuators, vol. 129, No. 2, pp. 151-158, Nov. 1991.

O'Keefe et al., "Cavity ring-down optical spectrometer for absorption measurements using pulsed laser sources," Review of Scientific Instruments, 59, 11 pages, 1988.

Sadeghi et al., "Cavity Ring Down Spectroscopy Applied to Plasma Diagnostics," Proc. Int. Symp. Laser-aided Plasma Diagnostics, 8 pages, Lake Tahoe, CA, Sep. 1999.

Schweber, "An Old Communications Problem Reoccurs in Optical-Communication-System Design—How it Works: Making the Laser Diode Tunable", *EDN*, Sep. 28, 2000, pp. 44-48, (www.ednmag.com).

Spence et al., "A laser-locked cavity ring-down spectrometer employing an analog detection scheme," Review of Scientific Instruments, vol. 71, No. 2, pp. 347-353, Feb. 2000.

Sze. "Physics of Semiconductor Devices." pp. 763-765, John Wiley & Sons, N. Y., 1982.

Tayebati et al., "Microelectromechanical tunable filter with stable half symmetric cavity," Electronics Letters, IEE Stevanage, GB, vol. 34, No. 20, pp. 1967-1968, Oct. 1998.

Tayebati et. al., "Widely Tunable Fabry-Perot Filters using High Index-contrast DBRs," Design and Manufacturing of WDM Devices, Dallas, Texas, Nov. 4-5, 1997, SPIE vol. 3234, pp. 206-218, 1998.

Yang et al., "Back-Illuminated GAN/AlGAN Heterojunction Photodiodes With High Quantum Efficiency and Low Noise," Applied Physics Letters, vol. 73, No. 8, Aug. 24, 1998, pp. 1086-1088, XP000777678.

Edwards, "Multiple-Traverse Absorption Cell Design," Journal of the Optical Society of America, vol. 51, No. 1, pp. 98-102, Jan. 1961.

Kurochkin et al., "Complex-Cavity Two-Mode CO2 Laser for Saturated Intracavity Absorption Spectroscopy," Optical Spectroscopy, vol. 68, No. 6, pp. 793-797, 1990.

Kurochkin et al., "Three-Mirror Cavity CO2 Laser for Intracavity Saturated-Absorption Spectroscopy," Optical Spectroscopy, vol. 65, No. 2, pp. 265-267, 1988.

Paul et al., "Cavity Ringdown Measures Trace Concentrations," Laser Focus World, pp. 71-80, Mar. 1997.

Richman et al., "Continuously Tunable, Single-Longitudinal-Mode, Pulsed Mid-Infrared Optical Parametric Oscillator Based on Periodically Poled Lithium Niobate," Optical Society of America, vol. 17, No. 7, pp. 1233-1239.

Scherer et al., "Infrared Cavity Ringdown Laser Absorption Spectroscopy (IR-CRLAS) in Low Pressure Flames," Applied Physics B., vol. 64, pp. 699-705, 1997.

Shimizu et al., "Stark Spectroscopy by 10μ Lasers Using a Multipath Cell," Journal of Applied Physics, vol. 46, No. 1, pp. 258-259, Jan. 1975.

Smirnov et al., "Dye Lasers Using a Three-Mirror Cavity with Lamp Excitation," 4 pages, 1981.

\* cited by examiner

CAVITY RING-DOWN SPECTROMETER HAVING MIRROR ISOLATION

This application claims the benefit of U.S. Provisional Patent Application Ser. No. 60/793,279, filed Apr. 18, 2006.

BACKGROUND

The present invention pertains to detectors and particularly to spectrometers. More particularly, the invention pertains to cavity ring-down spectrometers.

SUMMARY

The invention is a ring-down spectrometer having mirror isolation from a substance sampling cavity within the spectrometer.

DESCRIPTION

A cavity ring-down spectrometer (CRDS) may include a resonator cavity supporting a light path defined by a plurality of mirrors. The mirrors may guide light, which is supplied by a laser, for example, a tunable pumped laser, along the light path. A test or sample substance, or an analyte, such as a gas, air from an environment for instance like that of a battlefield, and so forth, may be introduced into the resonator cavity. The light, which could be a pulse of light or a continuous wave of light, may decay at a rate dependent upon the nature of the sample substance to be detected, and the rate of the decay is measured over time.

An aspect of the present invention may include keeping low vapor pressure gases and particulates in a gas sample from coating the optics which may degrade the base ring down time of an optical cavity ring down spectrometer.

For an empty cavity, the intensity of the light in the cavity may decrease exponentially at a ring-down rate that depends on the reflectivity of the mirrors, the separation between the mirrors, and the speed of light in the cavity. When the sample substance is introduced into the resonator cavity, the ring-down rate may accelerate. An absorption spectrum for the sample substance may be obtained by plotting the reciprocal of the ring-down rate versus the wavelength of the incident light. This absorption spectrum may be used to identify and/or analyze the sample substance and/or at least some of its characteristics.

The sample substance that is introduced into the resonator cavity may coat the mirrors that define the light path. Because the ring-down rate depends at least partially on the reflectivity of the mirrors, a coating of the mirrors may change that reflectivity and, therefore, change the ring-down rate, which introduces error into the identification of the sample substance and/or its characteristics.

The present invention may reduce this coating of the mirrors and, therefore, improve the accuracy of identifying the sample substance, properties, and/or its characteristics.

According to one aspect of the invention, a cavity ring-down spectrometer may have a structure, a mirror, and an isolator. The structure may form a resonator cavity, and the resonator cavity may include a sample sub-cavity and a mirror sub-cavity. The spectrometer may sense a substance entering or present in the sample sub-cavity. The mirror may be within the mirror sub-cavity, and the mirror may direct light through the sample sub-cavity and the mirror sub-cavity. The isolator may reduce, inhibit or prevent the substance in the sample sub-cavity from entering the mirror sub-cavity.

According to another aspect of the invention, a cavity ring-down spectrometer system may have a structure, first, second, and third mirrors, and first, second, and third isolators. The structure may form a resonator cavity including at least first, second, and third cavity legs. The first cavity leg may include a first sample sub-cavity, the second cavity leg may include a second sample sub-cavity, and the third cavity leg may include a third sample sub-cavity. The resonator cavity may further include first, second, and third mirror sub-cavities. The first mirror sub-cavity may be between the first and second sample sub-cavities, the second mirror sub-cavity may be between the second and third sample sub-cavities, and the third mirror sub-cavity may be between the third and first sample sub-cavities.

The spectrometer may sense corresponding first, second, and third substances entering the first, second, and third sample sub-cavities, respectively. The first mirror may be within the first mirror sub-cavity, the second mirror within the second mirror sub-cavity, and the third mirror within the third mirror sub-cavity. The first, second and third mirrors may direct light through the first, second and third sample sub-cavities and the first, second and third mirror sub-cavities.

The first isolator may reduce, inhibit or prevent the first and second substances in the first and second sample sub-cavities from entering the first mirror sub-cavity, the second isolator may reduce, inhibit or prevent the second and third substances in the second and third sample sub-cavities from entering the second mirror sub-cavity, and the third isolator may reduce, inhibit or prevent the third and first substances in the third and first sample sub-cavities from entering the third mirror sub-cavity.

According to still another aspect of the invention, an approach may include propagating light through a sample sub-cavity and a mirror sub-cavity of a resonator cavity, where the mirror sub-cavity contains a mirror that directs the light propagating through the sample sub-cavity and the mirror sub-cavity, sensing a ring-down rate of the light in response to a substance entering or present in the sample sub-cavity, and reducing, inhibiting or preventing migration of the substance from the sample sub-cavity to the mirror sub-cavity.

Figure 1:
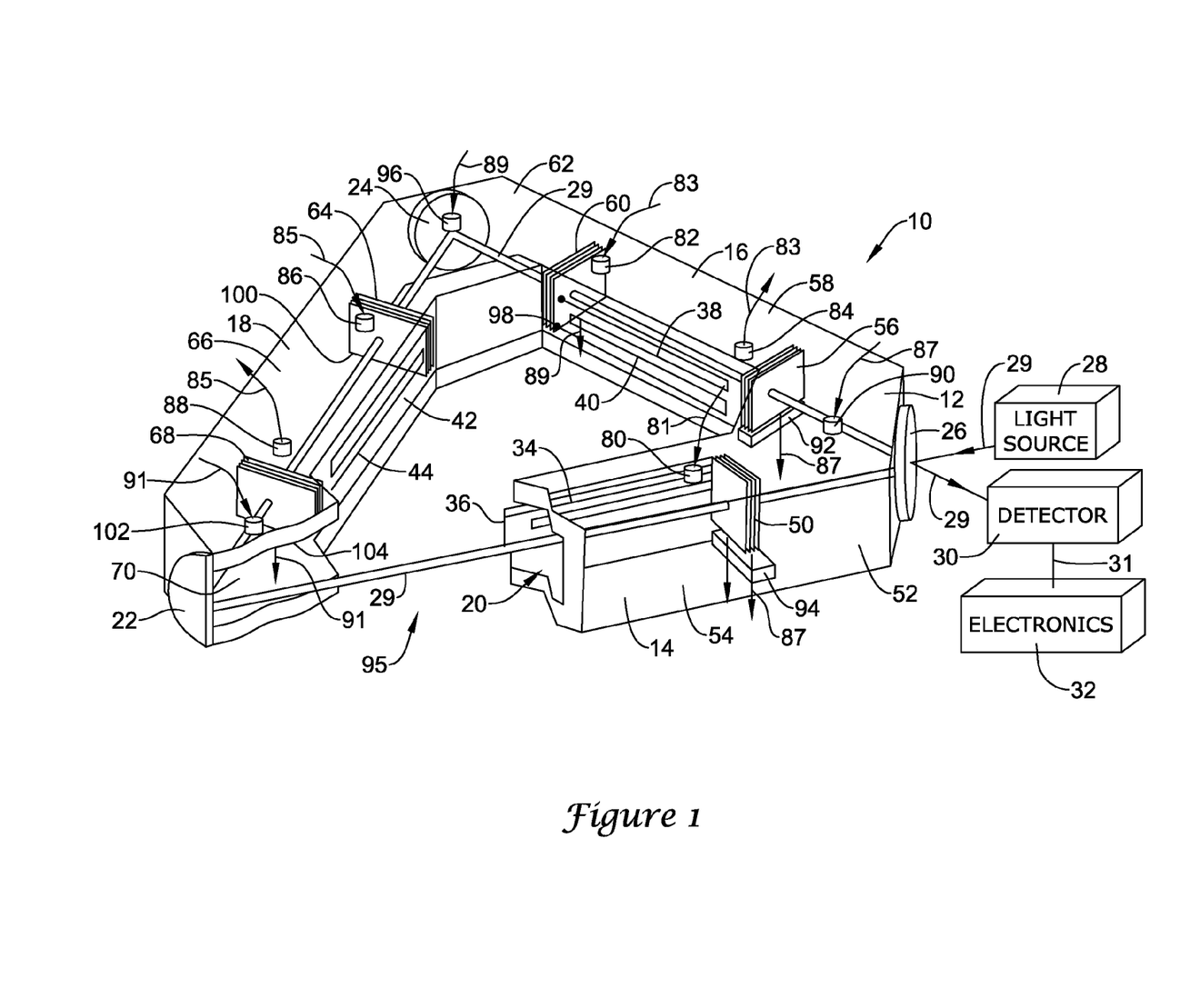
FIG. 1 is a isometric view of a cavity ring-down spectrometer according to an illustrative example of the present invention.

As shown in FIG. 1, a cavity ring-down spectrometer 10 may include a structure 12, such as a glass envelope, that has three legs 14, 16, and 18, and is hollow so as to define a resonator cavity 20. A mirror 22 may be located at the intersection between the legs 14 and 18, and a mirror 24 may be located at the intersection between the legs 16 and 18. The mirrors 22 and 24 are substantially fully reflective. A partially transmissive mirror 26 may be located at the intersection between the legs 14 and 16.

A light source 28, for example a pumped laser, may supply light 29 through the partially transmissive mirror 26 such that the light 29 from the light source 28 enters the resonator cavity 20 and is directed by the mirrors 22, 24, and 26 along the light path within the resonator cavity 20. A portion of the light 29 within the resonator cavity may emerge through the partially transmissive mirror 26 and be detected by a detector 30 which converts the light that it detects to an electrical signal 31 to be suitably processed by electronics 32.

A preconcentrator medium 34 may be situated or provided in the sample sub-cavity 54 in leg 14 of the resonator cavity 20 for adsorbing a sample substance. The medium or adsorber 34, for example, may contain a material targeted to a specific sample substance to be adsorbed. When the sample enters the sub-cavity 54, it may be adsorbed by the medium 34. The medium 34 may consist of carbon nano-tubes (CNT), coated nanowires, zeolites, and/or other items. Adjacent to the medium 34 may be a heater 36, such as a microheater, which can be attached to or provided on or in the preconcentration medium 34 in order to heat the medium 34 so as to desorb the sample such as a gas out of the medium or adsorber 34. A leg with its heater on may be considered as an activated leg. With some or all of the sample desorbed, light 29 may be propagated by source 28 into the cavity 20 and through the desorbed sample in the sub-cavity 54, with some of the light returning back out of the cavity 20 on to detector 30 for conversion to an electrical signal 31 to be processed by electronics 32 to determine the identity or properties of the sample in view of the ring-down characteristics of the light 29 affected by the sample in the sub-cavity 54. Heater 36 may be configured in a serpentine or other pattern. Various preconcentration medium/heater combinations and patterns may be used for adsorbing and desorbing the sample in the sub-cavity 54.

A preconcentrator medium 38 may be situated or provided in the sample sub-cavity 58 in leg 16 of the resonator cavity 20 for adsorbing a sample substance. The medium or adsorber 38, for example, may contain a material targeted to a specific sample substance to be adsorbed. When the sample enters the sub-cavity 58, it may be adsorbed by the medium 38. The medium 38 may consist of carbon nano-tubes (CNT), coated nanowires, zeolites, and/or other items. Adjacent to the medium 38 may be a heater 40, such as a microheater, which can be attached to or provided on or in the preconcentration medium 38 in order to heat the medium 38 so as to desorb the sample such as a gas out of the medium or adsorber 38. With some or all of the sample desorbed, light 29 may be propagated by source 28 into the cavity 20 and through the desorbed sample in the sub-cavity 58, with some of the light returning back out of the cavity 20 on to detector 30 for conversion to an electrical signal 31 to be processed by electronics 32 to determine the identity or properties of the sample in view of the ring down characteristics of the light 29 affected by the sample in the sub-cavity 58. Heater 40 may be configured in a serpentine or other pattern. Various preconcentration medium/heater combinations and patterns may be used for adsorbing and desorbing the sample in the sub-cavity 58.

A preconcentrator medium 42 may be situated or provided in the sample sub-cavity 66 in leg 18 of the resonator cavity 20 for adsorbing a sample substance. The medium or adsorber 42, for example, may contain a material targeted to a specific sample substance to be adsorbed. When the sample enters the sub-cavity 66, it may be adsorbed by the medium 42. The medium 42 may consist of carbon nano-tubes (CNT), coated nanowires, zeolites, and/or other items. Adjacent to the medium 42 may be a heater 44, such as a microheater, which can be attached to or provided on or in the preconcentration medium 42 in order to heat the medium 42 so as to desorb the sample such as a gas out of the medium or adsorber 42. With some or all of the sample desorbed, light 29 may be propagated by source 28 into the cavity 20 and through the desorbed sample in the sub-cavity 66, with some of the light returning back out of the cavity 20 on to detector 30 for conversion to an electrical signal 31 to be processed by electronics 32 to determine the identity or properties of the sample in view of the ring-down characteristics of the light 29 affected by the sample in the sub-cavity 66. Heater 44 may be configured in a serpentine or other pattern. Various preconcentration medium/heater combinations and patterns may be used for adsorbing and desorbing the sample in the sub-cavity 66.

The preconcentration media 34, 38, and 42 may be targeted to the same sample substance or may be individually targeted to different sample substances. There need only be one of the media 34, 38, and 42 associated with the cavity ring-down spectrometer 10. However, there may be more or less than the number of the media 34, 38, and 42 associated with the cavity ring-down spectrometer 10.

A baffle 50 may divide a mirror sub-cavity 52 and a sample sub-cavity 54 of the resonator cavity 20 from each other. The mirror sub-cavity 52 may contain the partially transmissive mirror 26, and the sample sub-cavity 54 may contain the medium 34. The baffle 50, for example, may have one or more baffle plates.

A baffle 56 may divide the mirror sub-cavity 52 of the resonator cavity 20 from a sample sub-cavity 58 of the resonator cavity 20. The sample sub-cavity 58 may contain the medium 38. A baffle 60 may divide the sample sub-cavity 58 of the resonator cavity 20 from a mirror sub-cavity 62 of the resonator cavity 20. The mirror sub-cavity 62 may contain the mirror 24. Each of the baffles 56 and 60, for example, may have one or more baffle plates.

A baffle 64 may divide the mirror sub-cavity 62 of the resonator cavity 20 from a sample sub-cavity 66 of the resonator cavity 20. The sample sub-cavity 66 may contain the medium 42. A baffle 68 may divide the sample sub-cavity 66 of the resonator cavity 20 from a mirror sub-cavity 70 of the resonator cavity 20. The mirror sub-cavity 70 may contain the mirror 22. Each of the baffles 64 and 68, for example, may have one or more baffle plates.

An additional baffle (not shown in FIG. 1 because of an illustrative cutout portion 95 at leg 14) may divide the sample sub-cavity 54 and the mirror sub-cavity 70 of the resonator cavity 20 from each other. The additional baffle, for example, may have one or more baffle plates. The additional baffle of sub-cavity 54 may be like the other baffles of the sub-cavities 58 and 66. The leg 14 may have external and internal structures along with components similar to those of legs 16 and 18.

Each of the baffles 50, 56, 60, 64, 68, and the baffle (not shown) that divides the sample sub-cavity 54 and the mirror sub-cavity 70, may have a window 72 (for example in baffle 50 of FIG. 2) through which the light 29 from the light source 28 propagates. The window 72 in each of the baffles 50, 56, 60, 64, 68, and the baffle (not shown) between the sample sub-cavity 54 and the mirror sub-cavity 70, could be an aperture. Alternatively, for better isolation of the sub-cavities, the window 72 in each of the baffles 50, 56, 60, 64, 68, and the baffle (not shown) between the sample sub-cavity 54 and the mirror sub-cavity 70, could be glass or another transparent member to pass the light 29 from the light source 28.

The sample sub-cavity 54 may have an inlet port 80 to permit a sample substance 81 to enter the sub-cavity 54 and an outlet port (not shown) to permit the sample substance to exit the sample sub-cavity 54. The sub-cavity 54 may be exposed to the sample substance 81. A fan, impeller, or other mechanism (not shown) may be used as desired to circulate the sample substance 81 through the input port 80, through the sample sub-cavity 54, and out through the exit port.

Similarly, the sample sub-cavity 58 may have an inlet port 82 to permit a sample substance 83 to enter the sub-cavity 58 and an outlet port 84 to permit the sample substance 83 to exit the sub-cavity 58. The sample sub-cavity 58 may be exposed to the sample substance 83. A fan, impeller, or other mechanism (not shown) may be used as desired to circulate the sample substance 83 through the input port 82, through the sample sub-cavity 58, and out through the exit port 84.

Also, the sample sub-cavity 66 may have an inlet port 86 to permit a sample substance 85 to enter the sub-cavity 66 and an outlet port 88 to permit the sample substance 85 to exit the sub-cavity 66. The sample sub-cavity 66 may be exposed to the sample substance 85. A fan, impeller, or other mechanism (not shown) may be used as desired to circulate the sample substance 85 through the input port 86, through the sample sub-cavity 66, and out through the exit port 88.

The mirror sub-cavity 52 may have an inlet port 90 to permit an isolation substance 87, such as an inert gas, to enter the mirror sub-cavity 52 and outlet ports 92 and 94 to permit the isolation substance 87 to exit the mirror sub-cavity 52. A fan, impeller, or other mechanism (not shown) may be used as desired to circulate the isolation substance 87 through the input port 90, through the mirror sub-cavity 52, and out through the exit ports 92 and 94. The isolation substance 87, for example, may be argon (Ar). As desired, the outlet port 92 may be situated along and/or near the bottom of the baffle 56, and the outlet port 94 may be situated along and/or near the bottom of the baffle 50. The baffles 50 and 56 and the flow of isolation substance 87 through the mirror sub-cavity 52 may act as an isolator that isolates the mirror sub-cavity 52 from the substances in the sample sub-cavities 54 and 58 so as to reduce, inhibit or prevent the ingress of sample substances 81 and 83 into the mirror sub-cavity 52 and coating the partially transmissive mirror 26.

In an illustrative example of the invention, the isolation substances 87, 89 and 91, such as an inert gas, for instance, may be pumped or drawn through the mirror sub-cavities 52, 62, and 70, respectively. In another illustrative example, the pressure of the isolation substances in the mirror sub-cavities 52, 62, and 70 may be controlled with a pressure that is higher than the pressure of the sample substances 81, 83 and 85 in the sample sub-cavities 54, 58, and 66, respectively, in order to aid in the isolation between the corresponding mirror sub-cavities 52, 62, and 70 and sample sub-cavities 54, 58, and 66.

The mirror sub-cavity 62 may have an inlet port 96 to permit the isolation substance 89, such as an inert gas, to enter the mirror sub-cavity 62 and outlet ports 98 and 100 to permit the isolation substance 89 to exit the mirror sub-cavity 62. A fan, impeller, or other mechanism (not shown) may be used as desired to circulate the isolation substance 89 through the input port 96, through the mirror sub-cavity 62, and out through the exit ports 98 and 100. The isolation substance 89, for example, may be argon. As desired, the outlet port 98 may be situated along and/or near the bottom of the baffle 60, and the outlet port 100 may be situated along and/or near the bottom of the baffle 64. The baffles 60 and 64 and the flow of the isolation substance 89 through the mirror sub-cavity 62 as an isolator may isolate the mirror sub-cavity 62 from the sample substances 83 and 85 in the sample sub-cavities 58 and 66, respectively, so as to reduce, inhibit or prevent the ingress of the sample substances 83 and 85 into the mirror sub-cavity 62 and coating the mirror 24.

The mirror sub-cavity 70 may have an inlet port 102 to permit isolation substance 91, such as an inert gas, to enter the mirror sub-cavity 70 and outlet ports such as an outlet port 104 to permit the isolation substance 91 to exit the mirror sub-cavity 70. A fan, impeller, or other mechanism (not shown) may be used as desired to circulate the isolation substance 91 through the input port 102, through the mirror sub-cavity 70, and out through the outlet ports such as the outlet port 104 and another outlet port (not shown). The isolation substance 91, for example, may be argon. As desired, the outlet port 104 may be situated along and/or near the bottom of the baffle 68, and the other outlet port (not shown) may be situated along and/or near the bottom of the other baffle (not shown) separating the mirror sub-cavity 70 from the sample sub-cavity 54. The baffles defining the mirror sub-cavity 70 and the flow of isolation substance 91 through the mirror sub-cavity 70 may act as an isolator that isolates the mirror sub-cavity 70 from the sample substances 85 and 81 in the sample sub-cavities 66 and 54, respectively, so as to reduce, inhibit or prevent the ingress of the sample substances 85 and 81 into the mirror sub-cavity 70 and coating the mirror 22.

Figure 2:
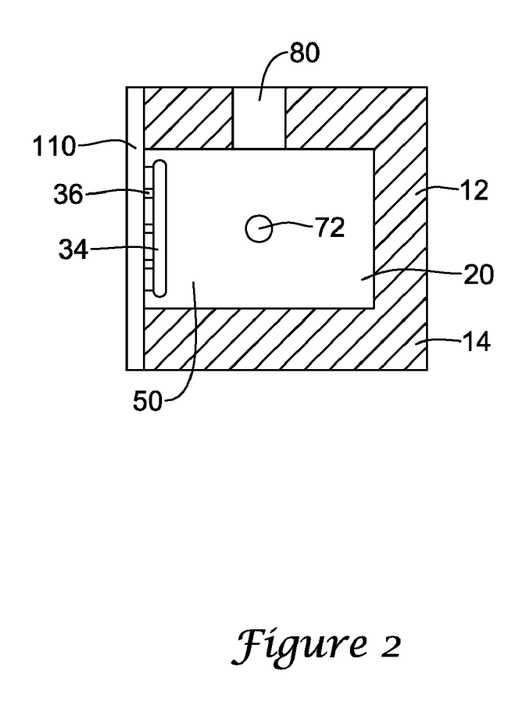
FIG. 2 is a cross-sectional view of a leg of the cavity ring-down spectrometer of FIG. 1.

As shown in FIG. 2, a cover 110 may be provided to cover an opening through the inside wall of the leg 14. This opening may be used to insert the baffle 50 that separates the mirror sub-cavity 52 and the sample sub-cavity 54 and to insert the baffle (not shown) that separates the sample sub-cavity 54 and the mirror sub-cavity 70. These baffles may be suitably attached to the walls of the resonator cavity 20 such as by use of a bonding agent. The medium 34 with its heater 36 may be suitably attached to these baffles or to the cover 110 or to both. The cover 110 is attached to the leg 14 so as to seal the sample sub-cavity 54. Similar covers may also be provided in the same manner for the legs 16 and 18 of the structure 12.

In one illustrative example, the cover 110 may be fabricated from the same material as is used for the structure 12. This material may be glass such as high temperature glass. In another illustrative example, the cover 110 may be fabricated from a different material than is used for the structure 12. Although not necessarily required, the different material may be thermally matched, relative to expansion and/or other properties, to the material used for the structure 12.

Figure 3:
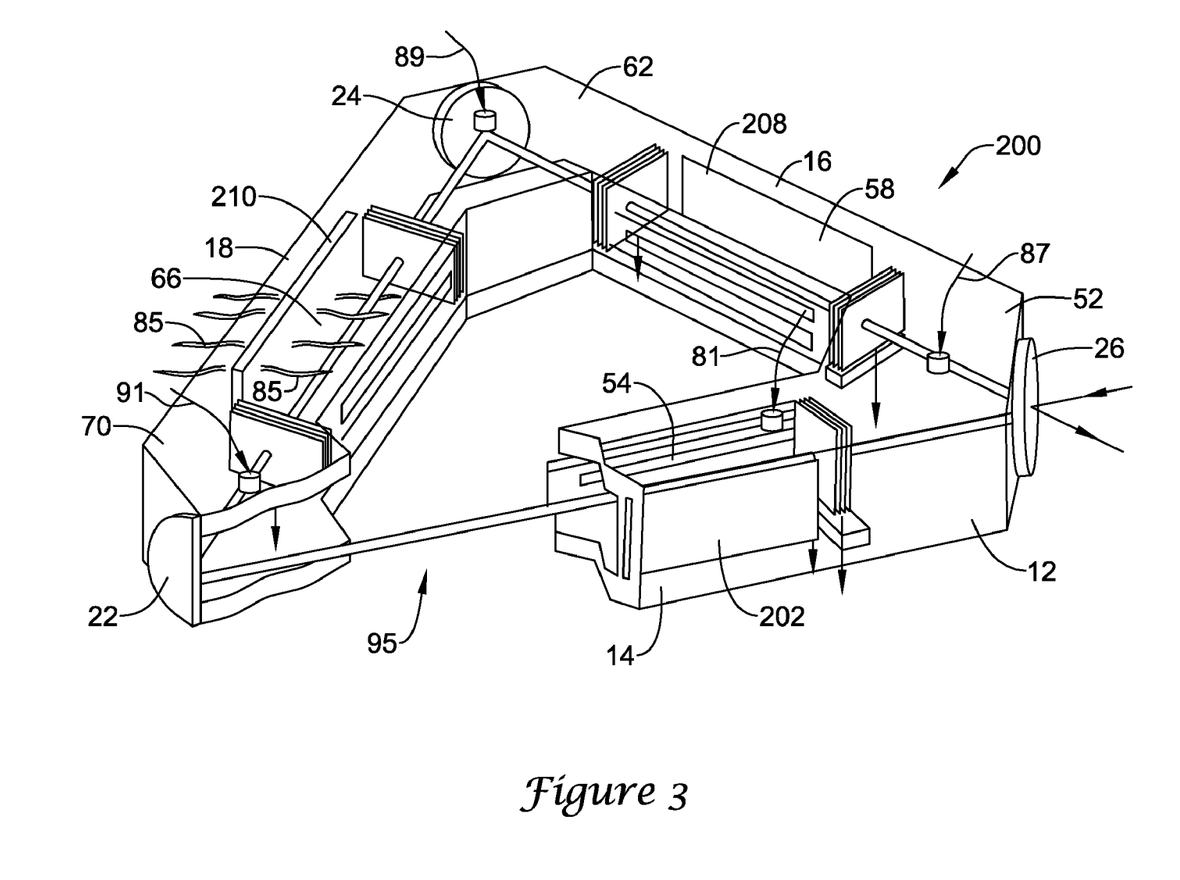
FIG. 3 is a isometric view of a cavity ring-down spectrometer according to another illustrative example of the invention.
Figure 4:
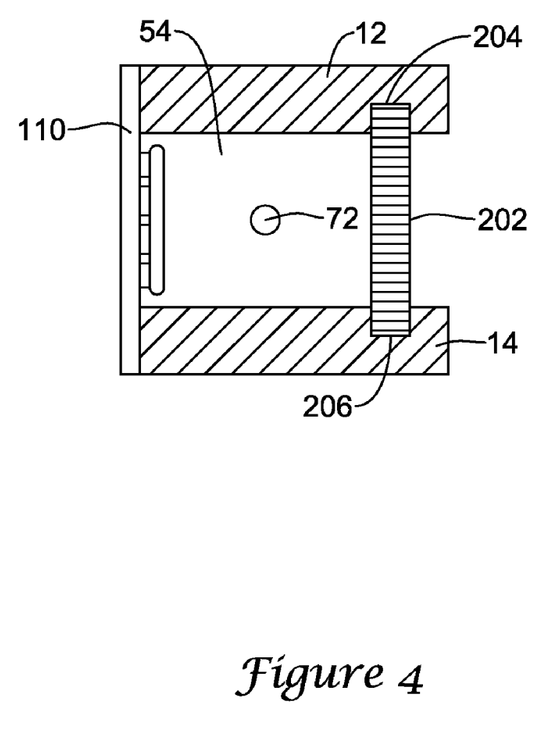
FIG. 4 is a cross-sectional view of a leg of the cavity ring-down spectrometer of FIG. 3.

FIGS. 3 and 4 show a cavity ring-down spectrometer 200 as another illustrative example of the invention. The cavity ring-down spectrometer 200 may be essentially the same as the cavity ring-down spectrometer 10 differing only in that the inlet and outlet ports 80, 84, 82, 86, 88, and a port of cavity 54 not shown, that permit sample substances to enter and exit their corresponding sample sub-cavities 54, 58 and 66 may be replaced by permeable membranes 202, 208 and 210 that permit bidirectional flow of sample substances into and out of the respective sample sub-cavities.

A permeable membrane 202 may be suitably affixed to the leg 14 so that it forms a wall of the sample sub-cavity 54. As shown in FIGS. 3 and 4, the permeable membrane 202 may be opposite to the cover 110, although the permeable membrane 202 could be mounted to any of the other sides of the structure 12. As shown in FIG. 4, the permeable membrane 202 may be secured in a slot 204 in the roof of the sample sub-cavity 54 and in a slot 206 in the floor of the sub-cavity 54. The sample sub-cavity 58 may be similarly provided with a permeable membrane 208, and the sample sub-cavity 66 may be similarly provided with a permeable membrane 210.

Certain modifications of the invention are discussed herein. For example, as shown in drawings, the cross-section of the structure 12 may be a hollow quadrilateral such that the cross-sections of the sample sub-cavities 54, 58, and 66 are also hollow quadrilaterals. However, these cross-sections could have other shapes as well.

Also, as disclosed herein, the baffles 50, 56, 60, 64, 68, and the baffle (not shown) between the sample sub-cavity 54 and the mirror sub-cavity 70, together with the flow of isolation substances 87, 89 and 91, such as an inert gas, through the mirror sub-cavities 52, 62, and 70, may form isolators that isolate the mirror sub-cavities 52, 62, and 70 from the sample substances 81, 83 and 85 in the sample sub-cavities 54, 58, and 66, respectively. Other kinds of isolators could alternatively be used to isolate the mirror sub-cavities 52, 62, and 70 from the sample substances 81, 83 and 85 in the sample sub-cavities 54, 58, and 66, respectively. For example, tight seals could be provided around the baffles, and the windows 72 could be fabricated from a material to enhance these seals. A combination of various approaches may be used to isolate mirror sub-cavities from sample sub-cavities.

The cavity ring-down spectrometers 10 and 200 are shown with the three legs 14, 16, and 18, as an illustrative example. However, the cavity ring-down spectrometer 10 or 200 may be implemented with any number of legs, including just one leg.

Figure 5:
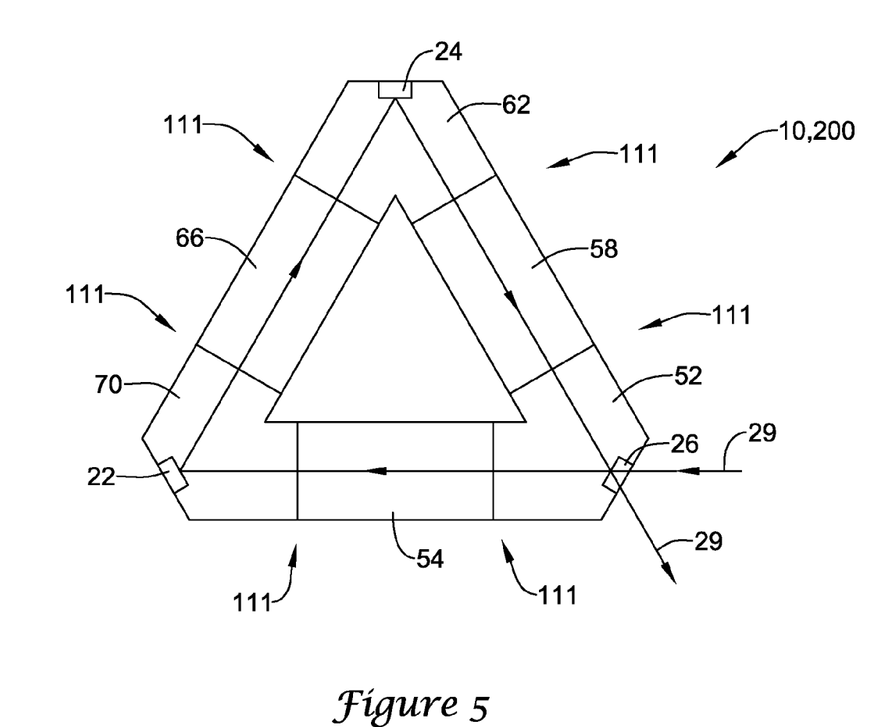
FIG. 5 relates to various approaches for reducing affects on optics of the cavity ring-down spectrometer.

As noted herein, a gas to be tested may be introduced into an absorption region (54, 58, 66) of cavity ring-down spectrometer 10, 200. Clean argon or other inert gas may be introduced into the mirror region (52, 62, 70). The two regions may be separated by a series of baffles with a hole or holes (with gas-tight windows) in each baffle to permit radiation to pass through the cavity ring-down spectrometer. Gas from the baffles may flow out through the bottom of the spectrometer block. The sample substance or gas may flow significantly through an outlet but may also pass through the openings below the baffle. Such configuration may prevent particulates and low vapor pressure gases from passing into the mirror region where the optics could be coated. However, a number of mechanisms 111 (FIG. 5) may be introduced to reduce affects on the mirror optics of the spectrometer. For instance, a mechanism may be introduced in the aperture region to collect particulates. One mechanism 111 may include electrostatic precipitators where a voltage causes the particles to be directed towards the outlet. Another mechanism 111 may include a collection of low vapor pressure gases which could be a condenser which causes nearly all but the low vapor pressure mirror gas to be collected via condensation and then circulated back to the mirror chamber. Still another mechanism 111 may include having actuable MEMS optical valves in the path length to only open up the cavity after the gas is present and when the cavity is ready to be pumped with laser radiation. A decreased exposure duty cycle may improve the lifetime of the spectrometer.

In the present specification, some of the matter may be of a hypothetical or prophetic nature although stated in another manner or tense.

Although the invention has been described with respect to at least one illustrative example, many variations and modifications will become apparent to those skilled in the art upon reading the present specification. It is therefore the intention that the appended claims be interpreted as broadly as possible in view of the prior art to include all such variations and modifications.

What is claimed is:

1. A cavity ring-down spectrometer comprising:
   resonator cavity;
   a first sub-cavity situated in the resonator cavity;
   a second sub-cavity situated in the resonator cavity;
   a mirror situated in the first sub-cavity;
   a space for a sample substance situated in the second sub-cavity; and
   an isolator situated in the resonator cavity to reduce movement of a substance from one sub-cavity to another sub-cavity.

2. The spectrometer claim 1, wherein:
   the mirror is arranged to direct light through the first and second sub-cavities; and
   the second sub-cavity is arrangeable for having a sample substance in a path of the light.

3. The spectrometer of claim 1, wherein the isolator provides for a flow of an isolation substance through the first sub-cavity.

4. The spectrometer of claim 1, wherein the isolator comprises a baffle between the first sub-cavity and the second sub-cavity.

5. The spectrometer of claim 4, wherein:
   the first sub-cavity comprises an inlet port and an outlet port;
   the inlet port is arranged to permit the isolation substance to flow into the first sub-cavity; and
   the outlet port is arranged to permit the isolation substance to flow out of the first sub-cavity.

6. The spectrometer of claim 4, wherein the baffle includes a window to permit the light to propagate through the first and second sub-cavities.

7. The spectrometer of claim 1, wherein the second sub-cavity comprises a preconcentration medium and a heater.

8. The spectrometer of claim 2, wherein the second sub-cavity includes a permeable membrane to permit the sample substance to enter the second sub-cavity.

9. The spectrometer of claim 2, wherein the pressure in the first sub-cavity is greater than the pressure in the second sub-cavity.

10. A sensing method comprising:
    propagating light through a mirror sub-cavity and a sample sub-cavity of a resonator cavity;
    sensing a ring-down rate of the light in response to a sample substance entering the sample sub-cavity; and
    reducing migration of the sample substance from the sample sub-cavity to the mirror sub-cavity.

11. The method of claim 10, wherein the reducing of migration of the sample substance from the sample sub-cavity to the mirror sub-cavity comprises a flowing an isolation substance through the mirror sub-cavity.

12. The method of claim 10, wherein the reducing of migration of the sample substance from the sample sub-cavity to the mirror sub-cavity comprises providing a pressure in the mirror sub-cavity that is greater than the pressure in the sample sub-cavity.

13. The method of claim 10, wherein:
    the reducing of migration of the sample substance from the sample sub-cavity to the mirror sub-cavity is provided by a baffle that separates the sample sub-cavity and the mirror sub-cavity from each other; and
    the baffle has a window for permitting propagation of the light between the sample sub-cavity and the mirror sub-cavity and for preventing a migration of the sample substance from the sample sub-cavity to the mirror sub-cavity.

14. The method of claim 10, wherein the sensing of a ring-down rate of the light in response to a sample substance entering the sample sub-cavity comprises sensing a ring-down rate of the light in response to a sample substance appearing in the sample sub-cavity by use of a preconcentration medium and a heater.

15. A spectrometer system comprising:
a structure forming a resonator cavity having at least first, seconds and third cavity legs; and
wherein:
the first cavity leg includes a first sample sub-cavity;
the second cavity leg includes a second sample sub-cavity;
the third cavity leg includes a third sample sub-cavity;
the resonator cavity further has at least a first mirror sub-cavity having a first mirror, a second mirror sub-cavity having a second mirror, and third mirror sub-cavity having a third mirror;
the first mirror sub-cavity is between the first and second sample sub-cavities;
the second mirror sub-cavity is between the second and third sample sub-cavities; and
the third mirror sub-cavity is between the third and first sample sub-cavities;
the first, second, and third sample sub-cavities are arranged to present corresponding first, second, and third substances;
the first, second, and third mirrors are arranged to direct light through the first, second, and third sample sub-cavities and the first, second, and third mirror sub-cavities; and,
a first isolator is arranged to reduce movement of the first and/or second substances from the first and second sample sub-cavities to the first mirror sub-cavity;
a second isolator arranged to reduce movement of the second and/or third substances from the second and third sample sub-cavities to the second mirror sub-cavity; and
a third isolator arranged to reduce movement of the third and/or first substances from the third and first sample sub-cavities to the third mirror sub-cavity.

16. The system of claim 15, wherein:
the first isolator comprises first and second baffles isolating the first mirror sub-cavity from the first and sample sub-cavities;
the second isolator comprises third and fourth baffles isolating the second mirror sub-cavity from the second and third sample sub-cavities;
the third isolator comprises fifth and sixth baffles isolating the third mirror sub-cavity from the third and first sample sub-cavities; and
each baffle has a window for transmission of light and prevention of substance migration.

17. The system of claim 15, wherein:
the first mirror sub-cavity comprises at least one inlet port and at least one outlet port;
the inlet port of the first mirror sub-cavity is arranged to permit an inert gas to flow into the first mirror sub-cavity;
the outlet port of the first mirror sub-cavity is arranged to permit an inert gas to flow out of the first mirror sub-cavity;
the second mirror sub-cavity comprises at least one inlet port and at least one outlet port;
the inlet port of the second mirror sub-cavity is arranged to permit an inert gas to flow into the second mirror sub-cavity;
the outlet port of the second mirror sub-cavity is arranged to permit an inert gas to flow out of the second mirror sub-cavity;
the third mirror sub-cavity comprises at least one inlet port and at least one outlet port;
the inlet port of the third mirror sub-cavity is arranged to permit an inert gas to flow into the third mirror sub-cavity; and
the outlet port of the third mirror sub-cavity is arranged to permit an inert gas to flow out of the third mirror sub-cavity.

18. The system of claim 15, further comprising:
a light source; and
a light detector; and
wherein:
the first mirror comprises a partially transmissive mirror;
the light source is arranged to direct light through the partially transmissive mirror and into the resonator cavity; and
the light detector is arranged to detect light emerging from the resonator cavity through the partially transmissive mirror.

19. The system of claim 15, wherein each of the first, second, and third sample sub-cavities comprises a respective preconcentration medium and a respective heater.

20. The system of claim 15, wherein:
the first sample sub-cavity includes a permeable membrane to permit the first substance to enter the first sample sub-cavity;
the second sample sub-cavity includes a permeable membrane to permit the second substance to enter the second sample sub-cavity; and
the third sample sub-cavity includes a permeable membrane to permit the third substance to enter the third sample sub-cavity.

* * * * *